United States Patent
Welle et al.

(10) Patent No.: US 10,564,026 B2
(45) Date of Patent: Feb. 18, 2020

(54) FILLING LEVEL MEASURING DEVICE WITH A FOLDABLE ANTENNA DEVICE

(71) Applicant: VEGA Grieshaber KG, Wolfach (DE)

(72) Inventors: Roland Welle, Hausach (DE); Levin Dieterle, Wolfach (DE)

(73) Assignee: VEGA GRIESHABER KG, Wolfach (DE)

( * ) Notice: Subject to any disclaimer, the term of this patent is extended or adjusted under 35 U.S.C. 154(b) by 258 days.

(21) Appl. No.: 15/108,765

(22) PCT Filed: Feb. 11, 2014

(86) PCT No.: PCT/EP2014/052626
§ 371 (c)(1),
(2) Date: Jun. 28, 2016

(87) PCT Pub. No.: WO2015/120879
PCT Pub. Date: Aug. 20, 2015

(65) Prior Publication Data
US 2016/0320225 A1    Nov. 3, 2016

(51) Int. Cl.
*G01F 23/284* (2006.01)
*G01F 1/80* (2006.01)
*G01N 11/14* (2006.01)

(52) U.S. Cl.
CPC .............. *G01F 23/284* (2013.01); *G01F 1/80* (2013.01); *G01N 11/14* (2013.01)

(58) Field of Classification Search
CPC ......... G01F 23/284; G01F 1/80; G01N 11/14; H01Q 1/08; H01Q 1/225
USPC ........................................................ 324/629
See application file for complete search history.

(56) References Cited

U.S. PATENT DOCUMENTS

| | | | | |
|---|---|---|---|---|
| 4,215,585 A | * | 8/1980 | Kunii | A61B 8/4281 367/104 |
| 5,777,573 A | * | 7/1998 | Klausing | G01S 13/9035 342/25 F |
| 6,634,234 B1 | | 10/2003 | Haas | |
| 8,711,049 B2 | * | 4/2014 | Fehrenbach | H01Q 19/08 333/254 |
| 2004/0108951 A1 | | 6/2004 | Edvardsson | |
| 2005/0248496 A1 | * | 11/2005 | Chen | H01Q 1/1228 343/766 |
| 2007/0014383 A1 | * | 1/2007 | Lam | H01Q 3/02 375/316 |
| 2008/0100501 A1 | | 5/2008 | Edvardsson | |

(Continued)

FOREIGN PATENT DOCUMENTS

| | | |
|---|---|---|
| CN | 1599864 | 3/2005 |
| DE | 195 00 324 | 5/1996 |

(Continued)

*Primary Examiner* — Jeff W Natalini
(74) *Attorney, Agent, or Firm* — Fay Kaplun & Marcin, LLP

(57) ABSTRACT

The invention relates to a fill level measurement device for determining a topology of a bulk material surface, comprising a foldable antenna assembly. The antenna assembly has a folded and an unfolded state. In the folded state, the antenna assembly can be pushed through a relatively small container opening when the measurement device is being fitted to a container. The antenna assembly is unfolded after the measurement device has been attached. This can make fitting less complex.

11 Claims, 4 Drawing Sheets

(56) References Cited

U.S. PATENT DOCUMENTS

2010/0019952 A1    1/2010  Poussin
2013/0277435 A1*   10/2013 Bielmann ........ G06K 19/07749
                                                        235/492

FOREIGN PATENT DOCUMENTS

DE    101 06 176       8/2002
EP       1451536       2/2011
KR    2008-0037552     4/2008

* cited by examiner

FILLING LEVEL MEASURING DEVICE WITH A FOLDABLE ANTENNA DEVICE

FIELD OF THE INVENTION

The invention relates to determining the fill level, volume and mass of filling materials and bulk materials. The invention relates in particular to a corresponding measurement device for determining a topology of a bulk material surface, to the use of such a measurement device for determining the viscosity of a moving liquid, and to the use of such a measurement device for determining a mass flow of a bulk material on a conveyor belt.

BACKGROUND

Known fill level measurement devices or other measurement devices used in the field of monitoring objects or monitoring bulk material emit electromagnetic waves or ultrasound waves which are reflected at least in part on the surface of the filling material, bulk material or the corresponding object. The transmission signal which is reflected at least in part can then be received by the antenna assembly of the measurement device and analysed by the electronics connected thereto.

By scanning over the surface of the filling material or bulk material, it is possible to determine the topology of the surface. In the context of the present invention, "topology" is understood to mean the shape of the surface of the filling material or bulk material (or, more generally, of an object). In this context, the term "topography" can also be used.

Such measurement devices for determining the topology are often complex to produce, fit and operate.

SUMMARY OF THE INVENTION

An object of the invention is to provide a device for determining the topology of a bulk material surface which can be fitted in or on a container in a simple manner.

This object is achieved by the features of the independent claims. Developments of the invention can be taken from the dependent claims and from the following description.

A first aspect of the invention relates to a measurement device for determining a topology of a bulk material surface. The measurement device comprises a main body, a drive shaft, an antenna assembly and a rotation assembly. The drive shaft is fastened to the main body in a rotatably mounted manner. The rotation assembly is designed to rotatably fasten the antenna assembly to the drive shaft such that the antenna assembly can assume a folded state and an unfolded state.

This means that, in the folded state, the antenna unit can be pushed through a relatively small mounting opening when the measurement device is being mounted on or in a filling material container. This mounting opening comprises for example an internal thread (measuring 1½", for example), into which the measurement device is screwed. It is thus possible to significantly simplify mounting, because it is not necessary to first attach the measurement device without antenna on or in the container and then attach the antenna to the measurement device from inside the container.

During mounting or operation of the measurement device, the antenna can be moved out of the mounting position thereof into an operational position by means of the joint (rotation assembly). As a result, a smaller container opening than those used in known measurement devices can be used for mounting.

The folding mechanism of the antenna assembly therefore allows a measurement device having an antenna assembly which has relatively large physical dimensions to be mounted through a given small container opening.

According to an embodiment of the invention, the rotation assembly is designed to rotatably fasten the antenna assembly to the drive shaft such that an angle between the rotational axis of the drive shaft (i.e. the longitudinal shaft thereof) and a longitudinal extension of the antenna assembly can change after the measurement device has been attached to a bulk material container.

The rotation assembly can be designed such that it only allows the antenna assembly to rotate axially about an axis which is fixed relative to said rotation assembly.

According to a further embodiment of the invention, the rotation assembly is connected to the antenna assembly at a position which is not at the centre of gravity of the antenna assembly, such that the antenna assembly can be transferred from the folded state into the unfolded state merely by means of the centrifugal force that occurs when the antenna assembly is rotated by the drive shaft.

The measurement device having the antenna folded can be mounted on the container. In this case, the folded antenna can be pushed inside the container through the container opening. If the measurement device is then put into operation, the drive shaft begins to rotate, and therefore the antenna assembly is caused to rotate. Since the rotation assembly is not attached at the centre of gravity of the antenna, a torque produced by the centrifugal force acting on the antenna acts on the antenna as a result of the rotation. This torque results in the antenna assembly being moved out of the folded state into the unfolded state, in which the measurement can then be taken.

A spring mechanism or traction mechanism or another mechanism for unfolding the antenna is not required since it is the centrifugal force alone that ensures unfolding.

Conversely, according to a further embodiment of the invention, the rotation assembly can be connected to the antenna assembly at a position which is not at the centre of gravity of the antenna assembly such that, when the drive shaft is stationary (i.e. when the drive shaft is not rotating), the antenna assembly can be transferred from the folded state into the unfolded state merely by means of the gravitational force acting on the antenna assembly and by means of the associated torque.

For this to happen, a weight element can for example be fastened to the antenna assembly, which ensures that a torque acts on the antenna assembly when said assembly is not rotating and therefore when there are no centrifugal forces at work. This torque causes the antenna to fold.

If, however, the centrifugal forces are significantly high when the antenna is rotating, the torque acts in the opposite direction, and this causes the antenna to unfold.

According to a further embodiment of the invention, the measurement device comprises a flexible cover for the antenna assembly and the rotation assembly in order to protect the antenna assembly and the rotation assembly from becoming soiled. The flexible cover has sufficient transmissivity to measuring signals emitted by the antenna. This cover is for example a PTFE woven pouch.

According to a further embodiment of the invention, the measurement device further comprises a first and a second fastening flange. The first fastening flange is rigidly connected to the main body of the measurement device. The second fastening flange is arranged so as to be movable along the drive shaft and is pushed on the container along the drive shaft towards the first fastening flange during the procedure for mounting the measurement device such that said second fastening flange is located between the container flange and the first fastening flange once the measurement device is attached to the flange of the container.

According to a further embodiment of the invention, a traction element is provided which is fastened to the antenna assembly and is designed to transfer the antenna assembly from the folded state into the unfolded state.

The traction element may for example be a Bowden cable and is connected to the second fastening flange, and therefore this second fastening flange pulls on the traction element when said second flange moves towards the first fastening flange when the measurement device is being mounted on the container and thereby pulls the antenna assembly from the folded state into the unfolded state. The "traction element" may also be designed to exert a compressive force on the antenna assembly in order to transfer said antenna assembly from the unfolded state into the folded state.

According to a further embodiment of the invention, a lock is provided which keeps the antenna assembly in the unfolded state even if said assembly is not rotating. The lock can be released before the device is detached from the container. By way of example, the antenna then folds down into the folded state automatically or is folded down into the folded state by taking the measurement device out of the container opening.

According to a further embodiment of the invention, a drive unit for rotating the drive shaft and thus the antenna assembly about a rotational axis extending in the longitudinal direction of the drive shaft is provided.

According to a further embodiment of the invention, the antenna assembly comprises an array which is designed to emit and receive the measuring signal emitted by the antenna assembly. When the antenna assembly is in the unfolded state, the array is arranged in a plane that encloses an angle α other than 90 degrees with the rotational axis of the drive unit. The angle α is for example between 30 and 60 degrees, for example 45 degrees.

As a result, the measuring range of the antenna can be widened by combining with a rotation. The rotational axis of the drive shaft can for example be a vertical rotational axis when the antenna assembly is fitted in or on a container that contains the filling material.

The array is for example a one-dimensional array comprising a single column of radiator elements, of which one column extends in the longitudinal extension of the antenna assembly. Radiator elements are for example substantially two-dimensional flat patches. The radiator elements may also be provided in the form of radiators that have been designed in a different manner.

The array can also be a two-dimensional array having a plurality of parallel columns and a plurality of rows arranged perpendicularly thereto which are each made up of individual radiator elements. The columns of the array extend in the longitudinal direction of the antenna unit and the rows of the array extend in the transverse direction of the antenna unit. The radiator elements of each row of the array can be conductively interconnected.

According to another embodiment of the invention, the antenna assembly comprises a high-frequency unit for generating a measuring signal, the high-frequency unit being integrated in the antenna unit. The high-frequency unit can also be integrated in the drive unit.

According to a further embodiment of the invention, the antenna unit comprises an evaluation electronics which rotates together with the antenna assembly when the antenna assembly is caused to rotate by the drive unit.

The evaluation electronics is for example located on the rear face of the antenna assembly, i.e. on the side facing away from the filling material or bulk material.

According to a further embodiment of the invention, the evaluation electronics is integrated in the antenna assembly or in the drive unit.

According to a further embodiment of the invention, the measurement device is a fill level measurement device, for example a radar level indicator.

According to a further embodiment of the invention, the fill level measurement device obtains the power it requires for taking measurements by means of a two-wire connection, the two-wire line being designed to communicate, in particular output, at least one topology measured value or at least one measured value derived therefrom (e.g. the mass in the container). The fill level measurement device comprises for example a power supply and communications interface for connecting the fill level measurement device to a two-wire line, by means of which interface the fill level measurement device is supplied with the power required for the measurement operation and by means of which measured data can be transmitted to a remote control unit.

A further aspect of the invention specifies the use of a measurement device as described above and in the following for determining the viscosity of a moving liquid.

A further aspect of the invention specifies the use of a measurement device as described above and in the following for determining a mass flow of a bulk material on a conveyor belt.

Embodiments of the invention are described below with reference to the figures.

DETAILED DESCRIPTION OF EMBODIMENTS

The drawings are schematic and not to scale.

Where the same reference signs are used in different figures in the following description of the figures, they denote the same or similar elements. The same or similar elements may also be denoted by different reference signs, however.

The present invention is used in the field of fill level measurement devices, in particular when said measurement devices are designed to determine the topology of a filling material or bulk material surface.

Applications in the field of object monitoring are also possible. The determination of the mass and/or volume of freely accessible bulk material stockpiles is a further field of application.

Figure 1:
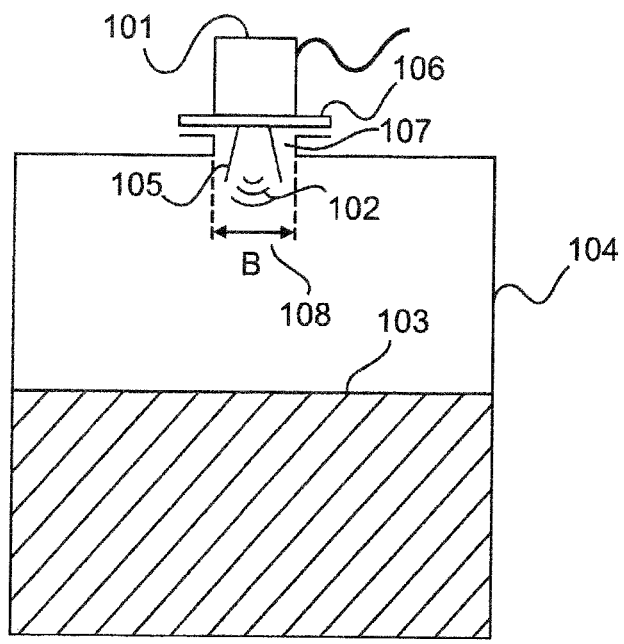
FIG. 1 shows a first fill level measurement device which is mounted on a container.

FIG. 1 shows a fill level measurement device 101 which records a representation of the reflectance in the container 104 by emitting a measuring signal 102, for example an electromagnetic measuring signal, towards a filling material surface 103.

The fill level measurement device 101 or at least the transmitting and/or receiving unit 105 is fastened to an existing opening 107 in the container by means of a mechanical adapter 106, for example a flange or a thread. The container opening 107 may have a mechanical extension B 108 which is large enough to allow at least the transmitting and/or receiving unit 107 of the fill level measurement device 101 to be inserted into the container 104.

Figure 2:
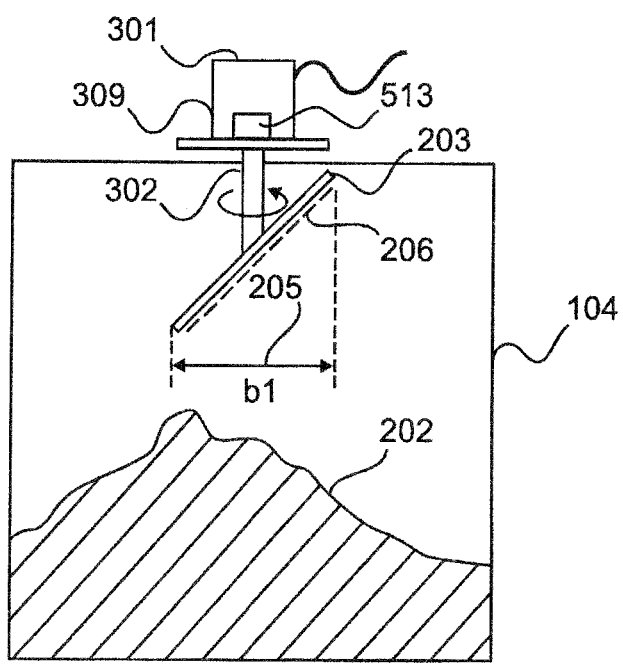
FIG. 2 shows a second fill level measurement device which is also fitted on a container.

FIG. 2 shows a fill level measurement device 301 which can measure the topology of the bulk material surface 202. For this purpose, the measurement device 301 has for example a one-dimensional antenna array 203 consisting of a plurality of radiator elements 206 arranged in a single column. The antenna array is used to emit and receive radar signals. An electronic beam steerer may be provided that can adjust the main emission and/or receiving direction of the antenna array.

In order to record the reflectance at different regions of the filling material surface 202, the transmitting and/or receiving unit (also referred to below as the "antenna assembly") is rotated by means of a drive shaft 302 driven by a drive unit 513. The transmitting and/or receiving unit 203 can have relatively large mechanical dimensions b1 205, which are generally larger than the dimensions of conventional container openings 108 (cf. FIG. 1).

As a rule, the antenna assembly 203 of the fill level measurement device is therefore only used in conjunction with containers or bulk material stock piles that are open at the top. Alternatively, the antenna assembly 203 is mounted on the main body 309 from inside the container after the main body 309 is mounted on the fastening flange of the container. This is complex and requires a fitter to access the inside of the container.

Figure 3:
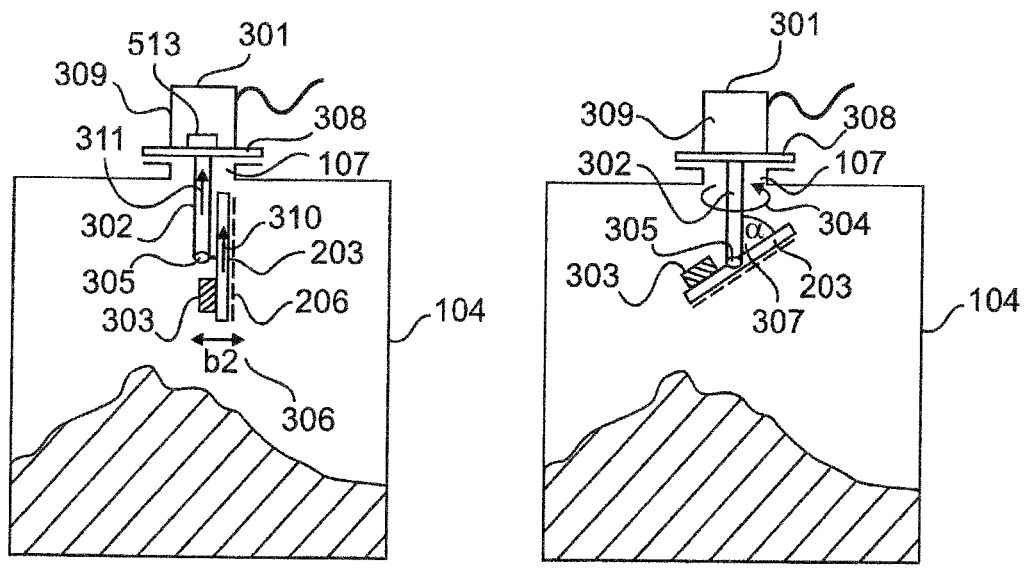
FIG. 3 shows a measurement device fitted on a container according to an embodiment of the invention.

FIG. 3 shows a measurement device according to an embodiment of the invention. The measurement device 301 comprises a main body 309 in which for example a drive unit 513 is arranged. A fastening flange 308 connecting the measurement device 301 to the container flange is located on the main body. A drive body 302 is connected to the main body, the rotational axis 311 of which is oriented vertically when the measurement device is fitted. A rotation assembly 305 is located at the end of the rotational shaft 302, by means of which rotation assembly the antenna assembly 203 is connected to the drive shaft 302. The arrow 310 indicates the longitudinal extension of the antenna assembly 203.

An array consisting of individual radiator elements 206, for example a one-dimensional array, is located on the lower face of the antenna assembly. A two-dimensional array may however also be provided, in which the radiator elements in each row are for example conductively interconnected.

The antenna unit 305 is rotatably mounted by means of the drive shaft 302 and encloses an angle α therewith other than 90°. It is particularly advantageous if an angle of 45° is produced which makes it possible to pick up signals from a wide portion of the container 308.

If an angular range of ±45° is measured using digital beam forming, by combining with the rotation of the antenna it is thus possible to measure the entire half-space containing the bulk material. Angles of <45° are also possible in order to avoid ambiguities during digital beam forming and to improve the resolution.

A plurality of transmitting and/or receiving elements are provided along the extension of the antenna. Each of these elements is capable of processing signals from different angular directions. Using known digital beam forming algorithms, the signals received individually by the elements can be used to change the main emission and/or receiving direction of the antenna assembly within a predetermined angular range. If an angular range of ±45° to the vertical main beam direction is selected for this, every point on the surface of the filling material can be measured by taking into account the rotation which is also occurring.

The arrangement advantageously combines the advantages of a mechanical change to the main beam direction (here: rotation) and those of an electronic beam sweep. As a result, it is possible to obtain extremely rapid measuring rates (for example less than 10 seconds) while having a mechanically simpler design (lower rotational speed, typically of approx. 60 min$^{-1}$) and significantly less complex electronics (for example owing to the one-dimensional structure of the antenna array). A number of m≤20 elements is generally sufficient for producing the one-dimensional array rows.

If, during the subsequent signal processing, the Doppler shift resulting from the antenna rotating is evaluated in the measuring signals picked up by the respective array elements, focusing in the transverse direction (radial direction ($X_A$-extension)) is significantly improved. For this purpose, known algorithms such as SAR (synthetic aperture radar) and ROSAR (rotor synthetic aperture radar, based on rotating antennae) can be used.

The antenna can for example consist of a one-dimensional antenna array having m individual elements. The individual elements can be formed as suitably designed printed circuit board patches or suitable waveguide ends or other known emission devices.

The signals reflected from the filling material surface are received by each of the radiator elements of the antenna array and are supplied separately to a digital evaluation unit. Said evaluation unit is for example housed in the drive unit. Using digital beam forming algorithms, the evaluation unit is capable of changing the main beam and/or receiving direction of the antenna, in particular by an angle of ±45° to the perpendicular 309 of the antenna unit, by combining these signals.

A weight element 303 can be provided on the rear face of the antenna assembly.

The measurement device comprises a drive shaft 302 which is slightly longer than the device of FIG. 2 and to which the transmitting and/or receiving element 203, also referred to as the "antenna assembly" or the "transmitting and/or receiving unit", is fastened by means of the rotation assembly 305, also referred to below as the "rotation element", such that said transmitting and/or receiving element can change its angle α 307 relative to the rotational shaft 302.

Installation into an existing container 104 is initially very simple because the mechanical dimensions of the fill level measurement device 301, and in this case in particular the transmitting and/or receiving unit 203, are reduced to a relatively small value b2 306 owing to the vertical orientation of the antenna assembly (i.e. the orientation of the longitudinal extension of the antenna assembly parallel to the longitudinal direction of the rotation assembly).

Since this value is smaller than the mechanical dimension B 108 of the container opening 117, it is possible to simplify the installation and mechanical fastening of the sensor 301. In particular, a threaded fastening or a flange fastening can be provided by the flange 308, without the need to subsequently install the antenna when fitting the measurement device to the container.

When the measurement device is put into operation, the antenna assembly 203 is caused to rotate by the rotating drive shaft 302. The speed-dependent centrifugal force that acts on the weight element 303 mounted on the antenna assembly 203 now results in the antenna assembly being deflected towards the operating angle α 307 required for the actual detection of the topology of the bulk material surface. When the measurement device 301 is no longer in operation, the gravitational force of the weight element 303 allows the antenna assembly 203 to return to its initial folded position, which allows the measurement device to be removed.

Figure 4:
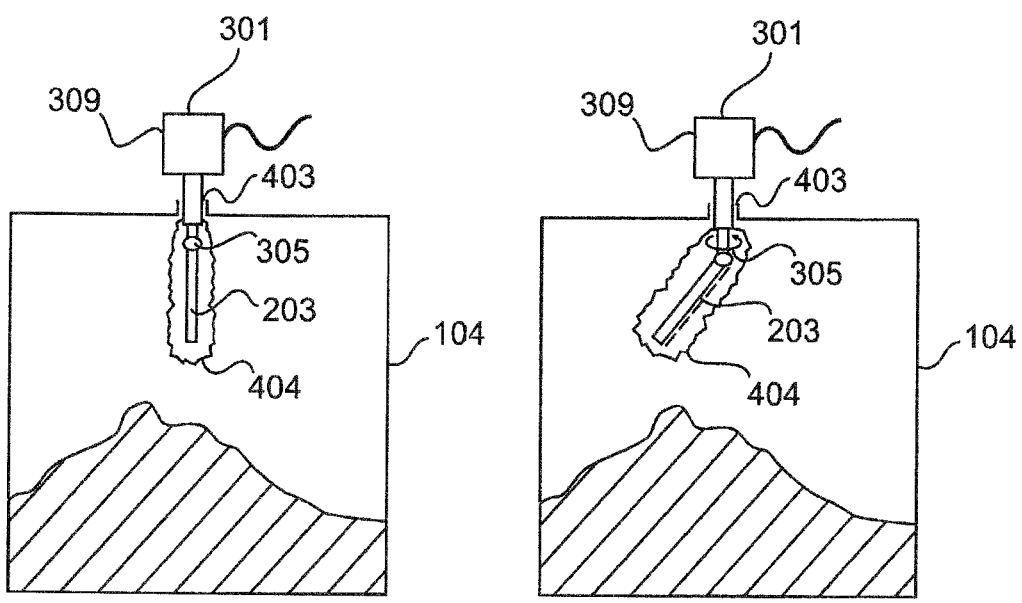
FIG. 4 shows a measurement device fitted on a container according to another embodiment of the invention.

FIG. 4 shows a further embodiment of a measurement device. The container 104 has a threaded opening 403 which has a diameter of 1½ or 2 inches, for example, and in which the fill level measurement device 301 can be mechanically fastened by screwing. In turn, the measurement device 301 has an antenna assembly 203 that can be moved by means of a revolute joint 305 and is deflected into the operating angle α 307 (referred to as the "unfolded state") once it has been put into operation. In order to protect the measurement device from becoming soiled, in particular the antenna assembly 203 and the rotation assembly designed as a revolute joint 305, a radome 404 can be provided which can for example be in the form of a PTFE woven pouch. The mechanical flexibility of the radome allows for mounting through an extremely small container opening 403.

Figure 5:
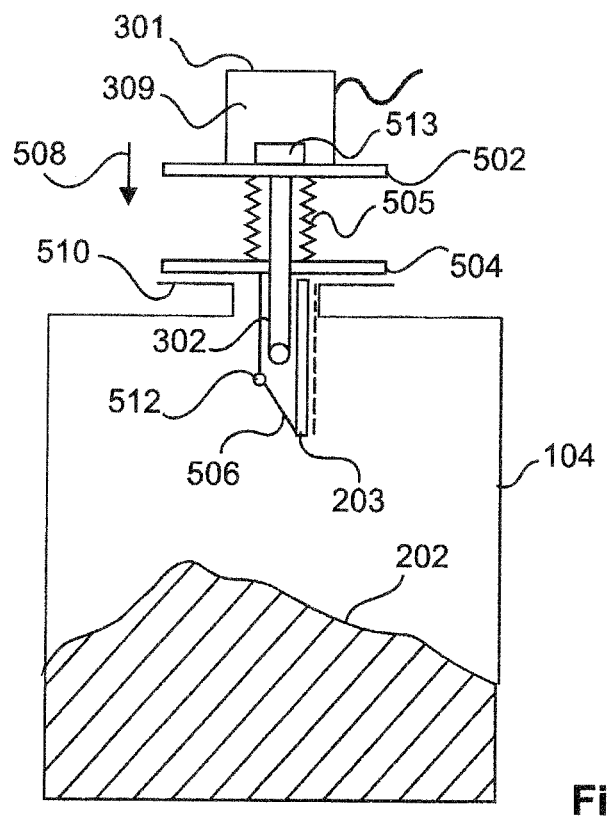
FIG. 5 shows a measurement device according to a further embodiment of the invention.
Figure 6:
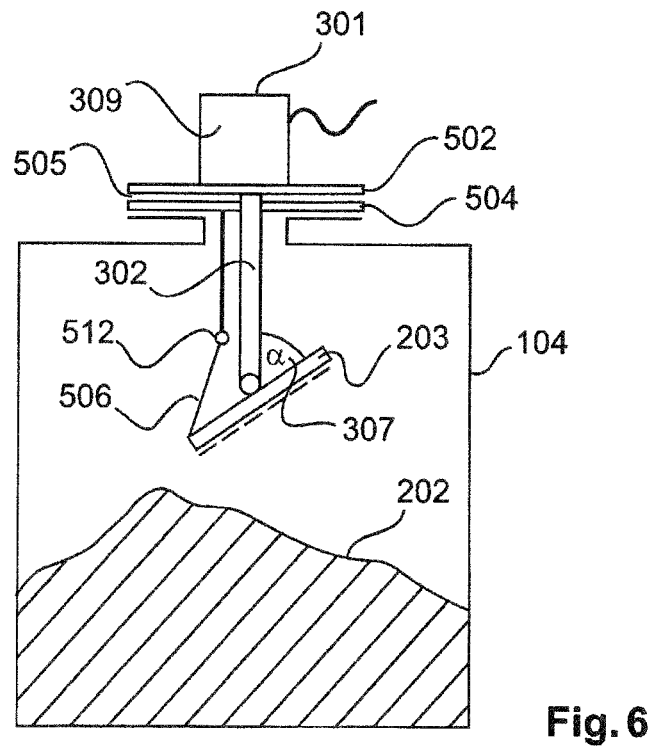
FIG. 6 shows the measurement device of FIG. 5, shown with the antenna arrangement unfolded.

In a further embodiment of the measurement device, the use of the centrifugal force in order to position the transmitting and/or receiving unit 203 when the measurement device is in the operational stage is completely dispensed with. FIGS. 5 and 6 show a corresponding embodiment.

FIG. 5 shows the measurement device 301 during the stage of being fitted on the container flange. The device 301 has a first flange 502 connected statically to the main body (housing) 309 of the measurement device, and a second fastening flange 504 which is movable along the drive shaft 203 and which is held in the removed state at a predefined distance from the static fastening flange 502 by means of a spring apparatus 505.

The second fastening flange 504 is connected to the rotatably mounted transmitting and/or receiving unit 203 by means of a traction element 506, which may comprise a deflection apparatus 512.

When the measurement device 301 is mounted on the container, a downward force (see arrow 508) towards the container flange 510 of the container 104 is generated. In this case, the antenna assembly 203 is moved into an operating angle α 307 by means of the deflection device 512, and this allows the measurement device 301 to operate in order to measure the topology of the surface 202 of the medium. The device is removed by reversing the sequence of operations, the spring mechanism 505 causing the antenna assembly 203 to return to the original position (folded state). This ensures that the measurement device can be removed without the antenna assembly having to be taken off first.

The traction element can for example be a traction rope or Bowden cable. In this case, in order to transfer the antenna assembly from the unfolded state (FIG. 6) into the folded state (FIG. 5), it is necessary for the gravitational force acting on the antenna to generate a corresponding torque which allows the antenna to fold up. This is achieved by the region of the antenna which tips downwards during folding being heavier than the region which tips upwards when the antenna is being folded.

Alternatively, the traction assembly can be designed such that it can exert not only a traction force, but also a compressive force.

Figure 7:
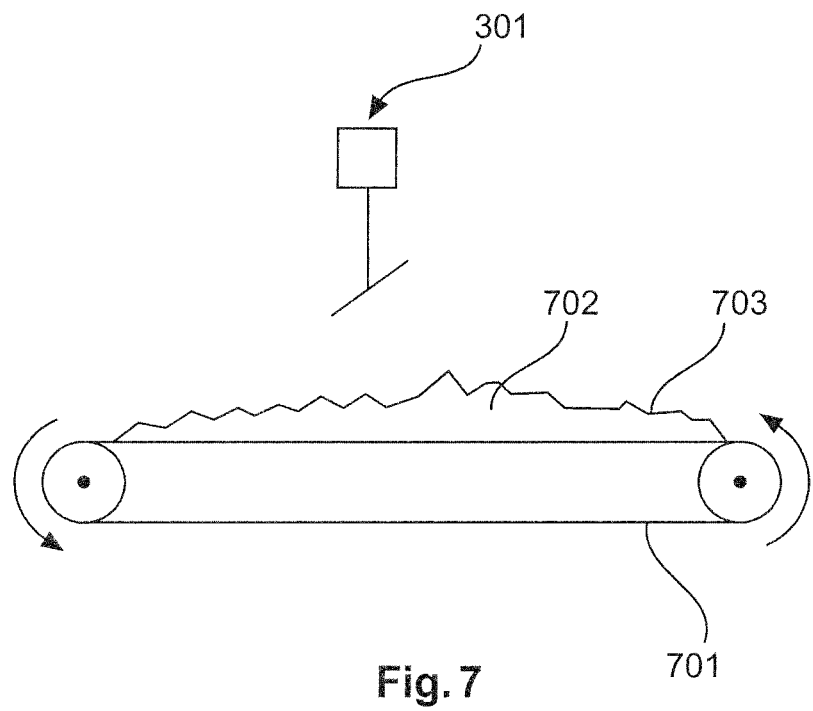
FIG. 7 shows a measurement device according to an embodiment of the invention for determining a mass flow of a bulk material on a conveyor belt.

FIG. 7 shows a conveyor belt 701 on which bulk material 702 is transported. The bulk material forms an irregular surface 703 which can be measured by the measurement device 301. The measurement device 301 may for example be a fill level measurement device, e.g. a radar level indicator, which can also calculate and output the fill level of a filling material, in addition to the topography of the bulk material surface. Overall, this device is capable of determining the mass flow of the bulk material on the conveyor belt.

Figure 8:
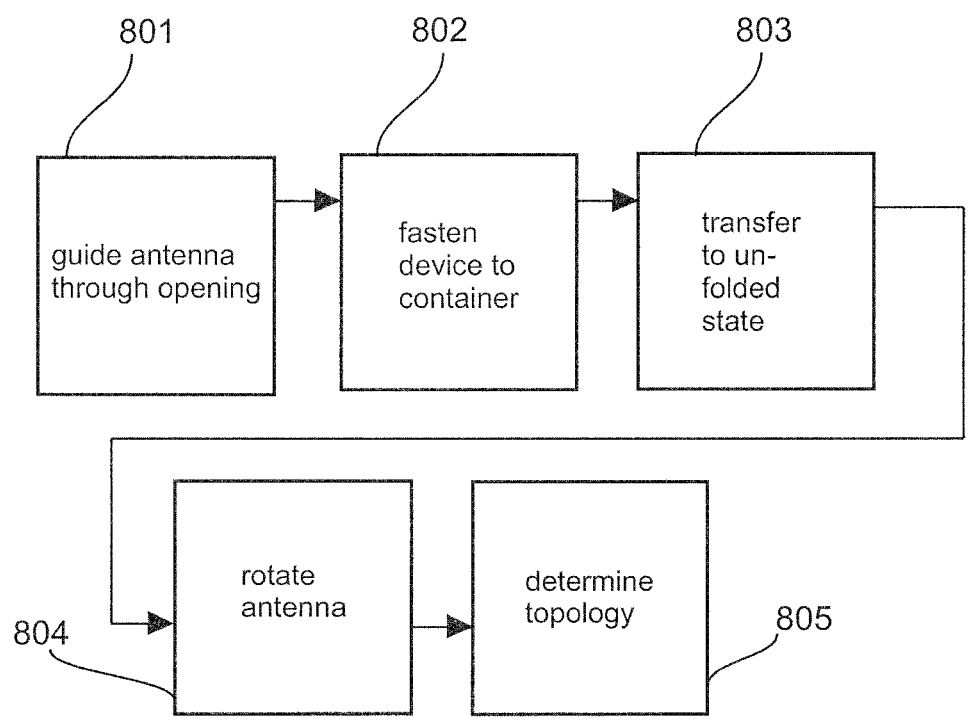
FIG. 8 shows a flow diagram of a method according to an embodiment of the invention.

FIG. 8 shows a flow diagram of a method according to an embodiment of the invention. In step 801, an antenna assembly attached to a drive shaft of a measurement device is guided through the opening in a filling material container. In step 802, the measurement device is fastened to the container and, in step 803, the antenna assembly is transferred from the folded state into the unfolded state. Then, in step 804, the antenna is caused to rotate by means of the drive shaft and, in step 805, the topology of the filling material surface is determined.

For completeness, it is pointed out that the terms "comprising" and "having" do not exclude any other elements or steps and "a" or "an" does not exclude a plurality. It should further be noted that features or steps described with reference to one of the above embodiments may also be used in combination with other features or steps of other above-described embodiments. Reference numerals in the claims should not be construed as limiting.

The invention claimed is:

1. A measurement device for determining a topology of a bulk material surface in a container, comprising:
a main body comprising a drive unit;
a vertical drive shaft having a first, upper end coupled to the drive unit and extending vertically to a second, lower end, a vertical rotation axis of the vertical drive shaft being defined by the first and second ends, the vertical drive shaft being configured to be rotated by the drive unit about the vertical rotation axis;
an antenna assembly comprising an array which is designed to at least one of emit or receive a measuring signal; and
a rotation assembly rotatably fastening the antenna assembly to the second, lower end of the drive shaft such that the antenna assembly can assume a folded state and an unfolded state;
wherein, the drive unit rotates the drive shaft and the antenna assembly about the vertical rotation axis,
wherein, when in the folded state, the antenna assembly is oriented in such a way that the antenna assembly is insertable or removable through an opening of the container, and
wherein, when in the unfolded state, the antenna assembly is oriented in such a way that the antenna assembly cannot be inserted or removed through the opening of the container.

2. The measurement device according to claim 1, wherein the rotation assembly is configured so that an angle between the rotational axis of the drive shaft and a longitudinal extension of the antenna assembly changes after the measurement device has been attached to the container.

3. The measurement device according to claim 1, wherein the rotation assembly is connected to the antenna assembly at a position which is not at the centre of gravity of the antenna assembly such that the antenna assembly is transferred from the folded state into the unfolded state merely by means of the centrifugal force that occurs when the antenna assembly is rotated by the drive shaft.

4. The measurement device according to claim 1, wherein the rotation assembly is connected to the antenna assembly at a position which is not at the centre of gravity of the antenna assembly such that, when the drive shaft is stationary, the antenna assembly is transferred from the unfolded state into the folded state merely by means of the gravitational force acting on the antenna assembly and by means of the associated torque.

5. The measurement device according to claim 1, further comprising:
   a flexible cover protecting the antenna assembly and the rotation assembly from becoming soiled.

6. The measurement device according to claim 1, comprising:
   a first fastening flange rigidly connected to the main body; and
   a second fastening flange arranged so as to be movable along the drive shaft and is located between a container flange of the container to which the measurement device is coupled and the first fastening flange once the measurement device is attached to the container flange.

7. The measurement device according to claim 1, further comprising:
   a traction element fastened to the antenna assembly and is designed to transfer the antenna assembly from the folded state into the unfolded state.

8. The measurement device according to claim 1, wherein the array is a one-dimensional array comprising a single column of radiator elements, of which one column extends in the longitudinal extension of the antenna assembly.

9. The measurement device according to claim 1, wherein the measurement device is a fill level measurement device.

10. The measurement device according to claim 1, wherein the device is configured to determine the viscosity of a moving liquid.

11. The measurement device according to claim 1, wherein the device is configured to determine a mass flow of a bulk material on a conveyor belt.

* * * * *